United States Patent [19]

Zimmer et al.

[11] Patent Number: 4,638,667
[45] Date of Patent: Jan. 27, 1987

[54] REMOTE PROBE POSITIONING APPARATUS

[75] Inventors: John J. Zimmer, Turtle Creek; Richard G. Soltesz, Gibsonia, both of Pa.

[73] Assignee: Westinghouse Electric Corp., Pittsburgh, Pa.

[21] Appl. No.: 572,498

[22] Filed: Jan. 20, 1984

[51] Int. Cl.⁴ ............................................. G01N 29/00
[52] U.S. Cl. .................... 73/432.1; 165/11.1; 414/8; 414/749; 414/751; 901/23; 901/24; 901/25; 901/44
[58] Field of Search .......................... 73/432 R, 432 B; 165/11 A; 414/8, 749, 751; 901/23, 24, 25, 44

[56] References Cited

U.S. PATENT DOCUMENTS 4,196,049  4/1980  Burns et al. ............................ 901/44
4,355,536 10/1982  McShane et al. ...................... 73/633

FOREIGN PATENT DOCUMENTS 2913742 10/1980  Fed. Rep. of Germany ........ 901/44
3042992  6/1982  Fed. Rep. of Germany .... 73/432 B
2519761  7/1983  France ............................ 165/11 A Primary Examiner—Peter Chin

[57] ABSTRACT

Apparatus for positioning a probe carried by an elongated flexible carrier includes a cantilevered telescoping extensible boom. A sprocketed tractor feed mounted at the distal end of the boom engages apertures in the carrier for feeding it and deflecting it from the boom in a direction substantially perpendicular to the longitudinal axis thereof. The tractor feed is mounted for rotational movement about the longitudinal axis of the boom. A withdrawal device engages the carrier adjacent to the supported end of the boom for reeling the carrier up into a cartridge. Extension and retraction of the boom is effected by a rack and pinion mechanism. Rotary resolvers measure the movement of the boom, the movement of the carrier with respect to the boom and the rotary movement of the tractor feed for providing signals to an associated microcomputer, accurately to detect and control the position of the probe. The microcomputer additionally provides on-line visualization of sludge profilometry and topography.

1 Claim, 7 Drawing Figures

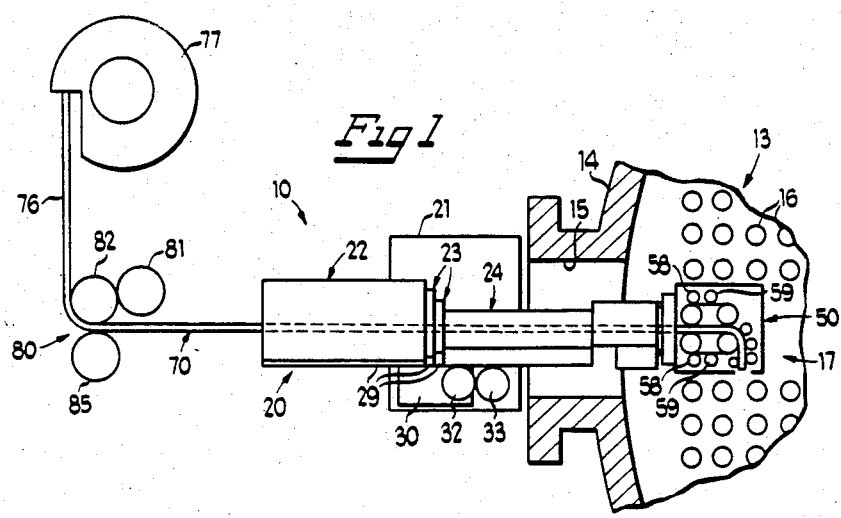
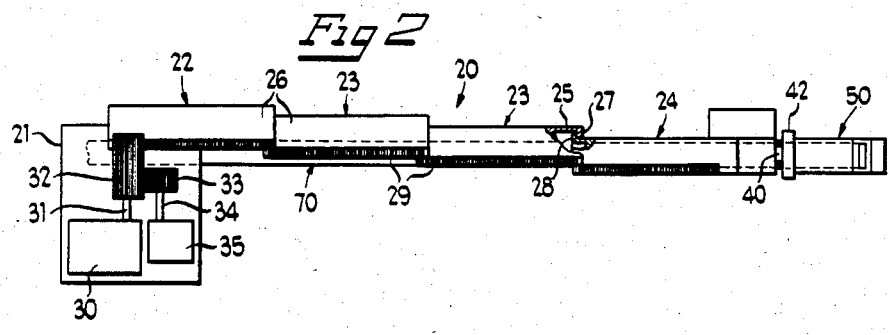
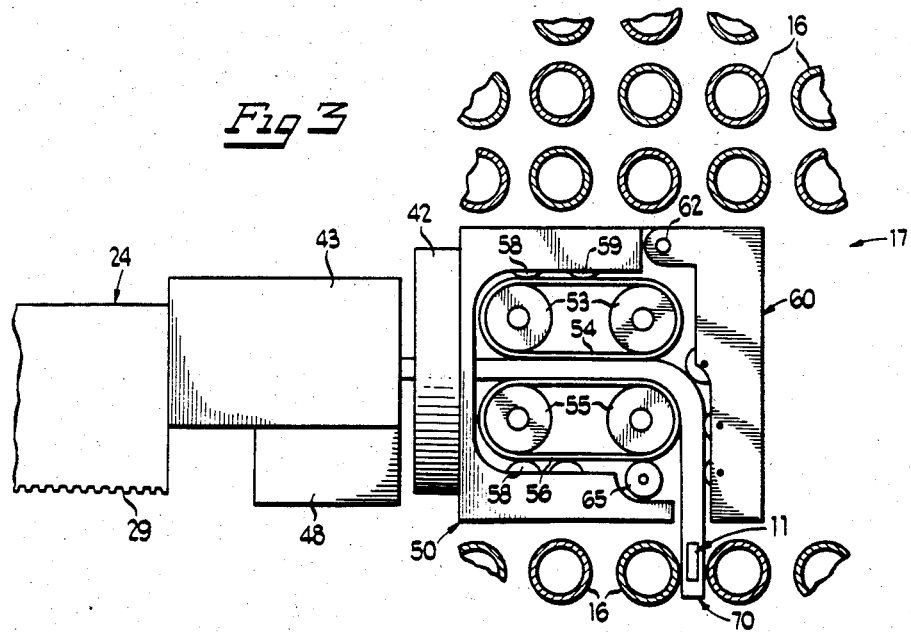

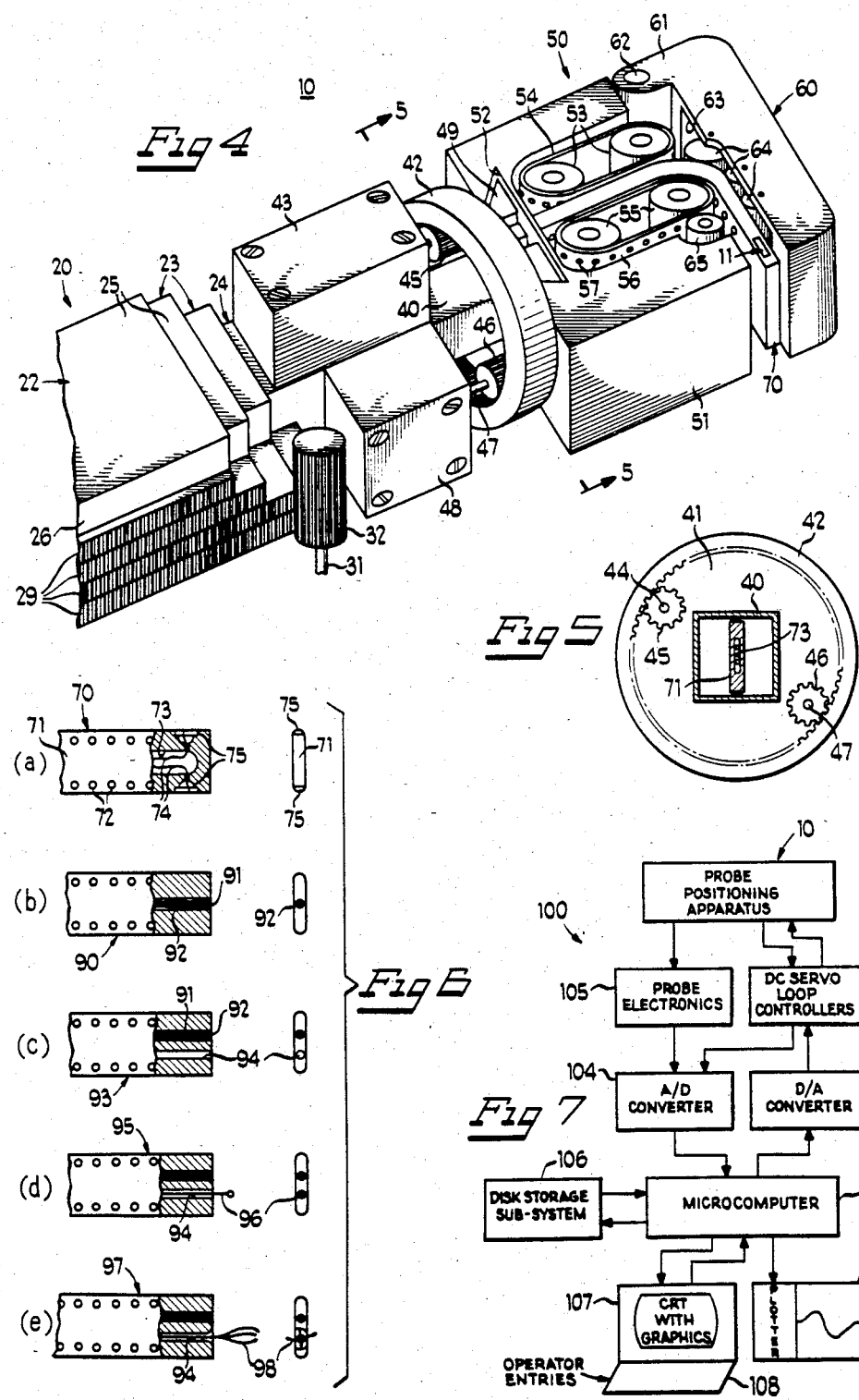

REMOTE PROBE POSITIONING APPARATUS

BACKGROUND OF THE INVENTION

The present invention relates generally to measuring and detecting apparatus capable of gathering data, and in particular to apparatus for delivering and positioning a sensing probe.

The invention has particular application to the maintenance of a steam generator, particularly a nuclear power plant steam generator.

A typical nuclear steam generator comprises a vertically oriented vessel, a plurality of U-shaped tubes disposed in the vessel so as to form a U-shaped tube bundle, and a tube sheet for supporting the tubes at the ends opposite the U-like curvature, and a dividing plate that cooperates with the tube sheet forming a primary fluid inlet plenum at the one end of the tube bundle and a primary fluid outlet plenum at the other end of the tube bundle. The primary fluid having been heated by circulation through the nuclear reactor core enters the steam generator through the primary fluid inlet plenum. From the primary fluid inlet plenum, the primary fluid flows upwardly through first openings in the U-tubes near the tube sheet which supports the tubes, through the U-tube curvature, downwardly through second openings in the U-tubes near the tube sheet, and into the primary fluid outlet plenum. At the same time, a secondary fluid, known as feedwater, is circulated around the U-tubes in heat transfer relationship therewith thereby transferring heat from the primary fluid in the tubes to the secondary fluid surrounding the tubes causing a portion of the secondary fluid to be converted to steam.

Material deposits tend to settle and accumulate between the tubes on the tube sheet at the bottom, forming a harmful sludge. Sludge profilometry is a method of measuring the heights of such sludge deposits in a nuclear steam generator through the use of a measurement probe, such as an ultrasonic probe, which is delivered between the rows of tubes of the steam generator.

One method of delivering the probe through the rows of tubes is disclosed in U.S. Pat. No. 4,355,536. In accordance with that method, an elongated track, rectangular in transverse cross section, is manually assembled in the steam generator vessel by piecing together track sections for extending the track through a handhole in the vessel wall and along the tube lane between the legs of the U-shaped tube bundle. This necessitates the presence of operating personnel in the steam generator vessel and consequent exposure to harmful radiation. A carriage is mounted for movement along the assembled track, the carriage including means for feeding a flexible probe carrier tape along the length of the track and then deflecting it laterally of the track in between the tube rows.

Operation of this prior profilometry system requires an operator at the handhole of the steam generator vessel to index the carriage along the track, while a second operator monitors and operates remote electronic readout equipment. Constant communication must be maintained between the handhole operator and the remote electronic equipment operator, because they must both operate the equipment in unison. This results in relatively slow run times. The data from the probe are recorded on a strip chart. The strip chart must then be later analyzed, resulting in a time consuming and costly procedure for placing the data in usable form. This off-line data analysis frequently means that the results of the tests are not available until several months after the data are collected.

SUMMARY OF THE INVENTION

It is a general object of the present invention to provide an improved apparatus for delivering and positioning a probe, which avoids the disadvantages of prior probe delivery systems while affording additional structural and operating advantages.

An important object of this invention is the provision of a probe positioning apparatus which is capable of positioning a probe within an enclosure without requiring the presence of operating personnel inside the enclosure.

In connection with the foregoing object, it is another object of this invention to provide a probe positioning apparatus which is supported entirely from outside the enclosure.

Still another object of this invention is the provision of a probe positioning apparatus of the type set forth which is remotely controllable by a single operator.

Yet another object of this invention is the provision of a probe positioning apparatus of the type set forth which permits movement of the probe in various directions.

Another object of this invention is the provision of a probe positioning apparatus of the type set forth which is automatically operable so as to afford rapid gathering of data in a form suitable for on-line analysis.

Still another object of this invention is the provision of a probe positioning apparatus of the type set forth, which affords precise and substantially error-free probe positioning.

Still another object of this invention is the provision for on-line visualization of sludge profilometry and topography which provides accurate and timely quantification of the sludge buildup.

These and other objects of the invention are attained by providing apparatus for positioning a probe within an enclosure defined by a vessel wall from outside the wall through an opening therein, the apparatus comprising: an elongated extensible boom supported outside of the vessel wall and having an end adapted for extension into and retraction from the enclosure through the opening therein, an elongated flexible carrier for the probe extending along the boom from outside the vessel wall, and carrier drive means including feed means mounted on the boom for movement therewith into and out of the enclosure, the drive means being coupled to the carrier for effecting movement thereof with respect to the boom for cooperation with the boom movement to position the probe.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there are illustrated in the accompanying drawings preferred embodiments thereof, from an inspection of which, when considered in connection with the following description, the invention, its construction and operation, and many of its advantages should be readily understood and appreciated.

FIG. 1 is a partially diagrammatic top plan view of a probe positioning apparatus constructed in accordance with and embodying the features of the present invention, and illustrating the use of the apparatus for inserting the probe through a handhole of a nuclear steam generating vessel, the apparatus being illustrated in a partially-extended position;

FIG. 2 is a side elevational view of the telescoping boom of the probe positioning apparatus of FIG. 1, with the boom illustrated in its fully extended position;

FIG. 3 is an enlarged, fragmentary view similar to FIG. 1, illustrating delivery of a probe between tube rows of a nuclear steam generator;

FIG. 4 is an enlarged, fragmentary, perspective view of the probe carrier feed mechanism of the present invention;

FIG. 5 is a view in vertical section taken generally along the line 5—5 in FIG. 4;

FIGS. 6(a)–6(e) are fragmentary, side elevational and end elevational views of several different embodiments of probe carrier tape for use with the present invention; and FIG. 7 is a block diagram of a data collection system utilizing the probe positioning apparatus of the present invention.

DESCRIPTION OF THE PREFERRED EMBODIMENTS

Referring to FIGS. 1 through 4 of the drawings, there is illustrated a probe positioning apparatus, generally designated by the numeral 10, for positioning, a probe 11 (see FIG. 4), such as an ultrasonic probe, within an enclosure such as a steam generator vessel 13 of the type utilized in a nuclear steam generating plant. The steam generator vessel 13 has a wall 14 which is provided with one or more handhole openings 15 therein (one shown) to provide access to the interior of the vessel 13. Disposed within the vessel 13 is a generally U-shaped tube bundle comprising a plurality of spaced-apart vertical tubes 16, the vertical portions of which are arranged in aligned rows and columns with a lane 17 between the legs of the U, all in a well known manner.

The probe positioning apparatus 10 includes an elongated extensible boom assembly 20 which is cantilevered from a support 21 disposed outside the steam generator vessel 13, so that the longitudinal axis of the boom assembly 20 is substantially in alignment with the axis of one of the handholes 15, as is best illustrated in FIG. 1. The boom assembly 20 comprises a plurality of nested telescoping sections including a base section 22, one or more intermediate sections 23 and a distal end section 24, each of the sections 22–24 being generally in the form of an inverted channel having a rectangular top wall 25 and a pair of depending parallel side walls 26. The top wall 25 of each of the sections 22 and 23 may be provided at the forward end thereof with a depending lip 27 disposed for engagement with an upstanding lug 28 at the rear end of the adjacent section disposed forwardly thereof, thereby to provide a coupling between adjacent sections (see FIG. 2). Each of the sections 22–24 is provided with a laterally outwardly extending rack flange 29.

Carried by the support 21 is a drive motor 30 having an output shaft 31 on which is mounted a pinion 32 disposed for meshing engagement with the racks formed by the rack flanges 29. When the boom assembly 20 is disposed in its fully contracted position, the forward end of the rack flange 29 of the distal end section 24 is disposed in engagement with the pinion 32. When the drive motor 30 is rotated in a clockwise direction, as viewed in FIG. 1, the distal end section 24 is extended to the right, as viewed in FIGS. 1 and 2. The rear end of each of the rack flanges 29 overlaps the forward end of the rack flange 29 of the adjacent section. Thus, when a section has been fully extended the pinion 32 will move into engagement with the rack flange 29 of the next section for extending it, until the boom assembly 20 has reached a fully extended position, illustrated in FIG. 2. For retraction of the boom assembly 20, the drive motor 30 is rotated in the opposite direction, whereupon the base section 22 is first returned to its normal rest position. As the base section 22 is retracted rearwardly, it pulls the other sections 23 and 24 with it, by reason of the interengagement of the lips 27 and lugs 28. When the base section 22 has been fully retracted, pinion 32 moves into engagement with the first intermediate section 23 and retracts it back into its normal position nested within the base section 22 and the process continues until the boom assembly 20 is fully retracted.

There is disposed in meshing engagement with the pinion 32 a gear 33 which is fixedly secured to a shaft 34 of an absolute resolver 35, mounted on the support 21. The resolver 35 operates in a well-known manner to convert the linear movement of the boom assembly 20 into a corresponding rotational angle, thereby to measure the extent of the linear movement.

Referring now also to FIG. 5 of the drawings, the forward end of the distal end section 24 is provided with an elongated coupling extension 40. On the forward end of the coupling extension 40 there is rotatably mounted by suitable means (not shown) a circular plate 41, disposed for rotation about an axis parallel to the longitudinal axis of the boom assembly 20. Integral with the circular plate 41 and projecting rearwardly therefrom around the entire circumference thereof is an annular ring gear flange 42 which is internally toothed, as is best illustrated in FIGS. 4 and 5. Mounted on the coupling extension 40 is a drive motor 43 having an output shaft 44 disposed substantially parallel to the longitudinal axis of the boom assembly 20 and carrying on the distal end thereof a gear 55 disposed in meshing engagement with the teeth of the ring gear flange 42 for effecting rotational movement thereof. Also disposed in meshing engagement with the ring gear flange 42 is a gear 45 fixedly secured to a shaft 47 of an absolute resolver 48 which is also mounted on the coupling extension 40, the resolver 48 measuring the circumferential linear travel of the ring gear flange 42 and thereby measuring the angle of rotation thereof.

Fixedly secured to the circular plate 41 and projecting forwardly therefrom are mounting studs 49 which are adapted for mounting on the boom assembly 20 a tractor feed unit, generally designated by the numeral 50. The tractor feed unit 50 has a box-like housing 51 provided at one end thereof with a coupling groove 52 (see FIG. 4) for mating engagement with the mounting studs 49, removably to mount the tractor feed unit 50 on the boom assembly 20. Rotatably mounted in the housing 51 are a first pair of rollers 53 spaced apart longitudinally of the boom assembly 20 and having entrained therearound an endless sprocket belt 54. Also rotatably mounted in the housing 51 is a second pair of rollers 55 which are also spaced apart longitudinally of the boom assembly 20, and have entrained therearound a second sprocket belt 56. Each of the sprocket belts 54 and 56 is provided with two rows of spaced-apart and outwardly projecting lugs 57, the facing reaches of the sprocket belts 54 and 56 being disposed substantially parallel to each other and spaced-apart a predetermined distance, all for a purpose to be explained more fully below. Also mounted in the housing 51 are two drive motors 58 diagrammatically shown in FIG. 1, respectively disposed for driving engagement with one of the rollers 53 and one of the rollers 55. Respectively associated with the drive motors 58 are two one-way clutches 59, so that the sprocket belt 54 is rotatable in a counterclockwise direction, and the sprocket belt 56 is rotatable in a clockwise direction, as viewed in FIGS. 3 and 4.

The tractor feed unit 50 is also provided with a deflector block 60 which is generally box-like in shape and is provided with a mounting leg 61 at one end thereof pivotally coupled to the housing 51 by a pivot pin 62. The deflector block 60 has a recess 63 formed in the side thereof facing the housing 51 for receiving a plurality of rotatably mounting idler rollers 64. Also mounted in the housing 51 is an absolute resolver 65 associated with one of the drive motors 58. In use, the deflector block 60 is pivotally movable between a normal closed position, illustrated in FIG. 4, and an open or threading position (not shown) pivoted away from the housing 51 in a counterclockwise direction, as viewed in FIG. 1.

Referring now also to FIG. 6(a), the probe 11 is transported by an elongated, flexible carrier tape, generally designated by the numeral 70. The tape 70 comprises an elongated flattened tape body 71 which preferably has substantial stiffness in the directions of its length and width, but it's bendable out of the plane defined by its length and width. The body 71 is provided with two rows of longitudinally spaced-apart sprocket holes 72, respectively disposed adjacent to the side edges thereof. The body 71 may be of unitary one-piece construction and is provided with a cavity 73 extending longitudinally thereof centrally thereof for accommodating the elongated conductors 74 of two ultrasonic transducers 75, which are disposed adjacent to the leading end of the tape body 71, respectively facing the lateral side edges thereof, as is best illustrated in FIGS. 4 and 6(a). A supply portion 76 of the carrier tape 70 is preferably wound on a supply spool or reel which may be formed as part of a supply cartridge 77 (see FIG. 1).

The probe positioning apparatus 10 also includes a tape withdrawing assembly, diagrammatically illustrated at 80 in FIG. 1. The tape withdrawing assembly 80 includes a drive motor 81 which drives, through a one-way clutch 82, a suitable sprocket (not shown) disposed for meshing engagement with the sprocket holes 72 of the carrier tape 70 for rotating the drive sprocket in a clockwise direction, as viewed in FIG. 1. The tape withdrawing assembly 80 also includes and absolute resolver 85 associated with the drive motor 81 for measuring the linear movement of the carrier tape 70 during withdrawal thereof.

In use, when the carrier tape 70 is threaded into the probe positioning apparatus 10, the leading end of the carrier tape 70 which houses and supports the probe 11 (in this case ultrasonic transducers 75) being fed through the retraction assembly 80 and thence through the boom assembly 20 to the tractor feed unit 50. More particularly, the carrier tape 70 is fed through the hollow sections 22-24 of the boom assembly 20, through the coupling extension 40 and into the tractor feed unit 50 between the sprocket belts 54 and 56. In this regard, it will be noted that the facing reaches of the sprocket belts 54 and 56 are spaced apart a distance so that the lugs 57 of both are disposed in driving engagement with the sprocket holes 72 of the carrier tape 70. The deflector block 60 is moved to its open or threading position to facilitate bending of the leading end of the carrier tape 70 around the forward end of the sprocket belt 56 and over the absolute resolver 65. The deflector block 60 is then pivoted back to its normal closed position illustrated in FIG. 4, wherein the idler rollers 64 are disposed in rolling engagement with the carrier tape 70 for cooperation with the sprocket belt 56 and the absolute resolver 65 to deflect the carrier tape 70 and guide it from the tractor feed unit 50 along an exit path disposed substantially perpendicular to the longitudinal axis of the boom assembly 20.

In operation, once the carrier tape 70 has been threaded through the probe positioning apparatus 10 in the manner described, the probe positioning apparatus 10 is disposed with the tractor feed unit 50 adjacent to the handhole 15 of the steam generator vessel 13 and the boom assembly 20 is extended by means of the drive motor 30 for moving the tractor feed unit 50 into the steam generator vessel 13 along the tube lane 17. As the boom assembly 20 is extended, the absolute resolver 35 measures the linear movement thereof. When the tractor feed unit 50 has reached the desired position, with the leading end of the carrier tape 70 positioned between two selected rows of tubes 16, the drive motors 58 of the tractor feed unit 50 are actuated for feeding the leading end of the carrier tape 70 and the probe 11 between the rows of tubes 16, as illustrated in FIG. 3. As the carrier tape 70 is fed, the supply portion 76 is pulled from the cartridge 77, the absolute resolver 65 measuring the linear movement of the carrier tape 70 with respect to the tractor feed unit 50. Thus, the position of the probe 11 can accurately be determined with respect to a reference position.

When it is desired to withdraw the carrier tape 70 from between the rows of tubes 16, the tape withdrawal assembly 80 is actuated for withdrawing the carrier tape 70 until the probe 11 has been withdrawn into the tractor feed unit 50 to substantially the position illustrated in FIG. 4. During this withdrawal, the linear movement of the carrier tape 70 is measured by the absolute resolver 85, so that just the right length of carrier tape 70 may be retracted into the cartridge 77. After this withdrawal, the boom assembly 20 then can be further extended or retracted to position the probe 11 for extension between another two rows of the tubes 16. When the tube rows on one side of the lane 17 have been probed, the tractor feed unit 50 is rotated through 180° by operation of the rotary drive motor 43 so that the tube rows on the other side of the lane 17 may be investigated in the same manner. In this regard, it will be noted that the absolute resolver 48 measures the angular movement of the tractor feed unit 50, so that it can be accurately stopped after 180° rotation.

While the probe positioning apparatus 10 has been described for use with an ultrasonic probe for sludge profilometry, it will be appreciated that the probe positioning apparatus 10 could also be used for positioning other types of probes. The carrier tape 70 could be suitably modified to accommodate the different types of probes, several of these alternative tape embodiments being illustrated in FIGS. 6(b)–(e). Thus, referring to FIG. 6(b), there is illustrated a tape 90 which has a small-diameter bore 91 extending longitudinally therethrough for accommodating therein a fiberscope 92. The fiberscope 92 may include fibers for transmitting light from a light source to the subject and other light fibers for returning reflected light to recordal equipment, all in a well known manner.

In FIG. 6(c), there is illustrated another alternative form of tape 93 which has two parallel bores extending therethrough, one being the bore 91 accommodating the fiberscope 92, and another bore 94 which may comprise a hydrojet channel for carrying fluid to the work site, such as for removing deposits and the like.

In FIG. 6(d), there is illustrated another form of tape 95 which is substantially identical to the tape 93, with the exception that the bore 94 receives therethrough a drill head 96.

In FIG. 6(e), there is illustrated a tape 97 which is substantially identical to the tape 95, with the exception that the bore 94 carries a retractor tool 98.

It will be appreciated that other modifications of the carrier tape 70 could be provided for other applications. Furthermore, it is noted that the tractor feed unit 50 is removable from the boom assembly 20 and could be replaced with another type of feed unit for handling other types of carriers. Such alternative feed units might be used, for example, in applications such as EDM tube cutting, vacuum removal of sludge from the tube lanes or the like.

It is an important feature of the present invention that it greatly facilitates the collection and analysis of probe data. Thus, referring to FIG. 7, the probe positioning apparatus 10 could be used as part of a data collection system, generally designated by the numeral 100, which includes a supervising microcomputer 101. Preferably, the motors 30, 43, 58 and 81 are DC servomotors with gear heads. Control of these motors is effected by the microcomputer 101 which transmits digital control signals through a digital-to-analog converter 102 to DC servo loop controllers 103 for controlling the operation of the various drive motors. Feedback signals from the resolvers associated with the several drive motors are fed in a feedback loop back to the DC servo loop controllers 103 and thence through an analog-to-digital converter 104 to the microcomputer 101. In this manner, precise positioning of the tractor feed unit 50 and the carrier tape 70 is possible, while at the same time eliminating the possibility of operator error. Furthermore, it will be appreciated that with the use of the present invention the probe 11 can be remotely positioned from outside the steam generator vessel 13, and the monitoring of the probe survey can be accomplished by a single operator.

The geometrical characteristics of the particular tube sheet being investigated may be stored in memory, either in the microcomputer 101 or in peripheral storage such as a disk storage sub-system 106. With the aid of this "map" of the tube sheet, and with the tractor feed unit 50 and the tape 70 starting from an initial predetermined reference position, the entire probe survey operation can be automatically conducted under microcomputer control.

As the probe survey is conducted, the data gathered by the probe 11 are fed from the probe positioning apparatus 10 to suitable probe electronics 105, such as ultrasonic electronics, and thence through the analog-to-digital converter 104 to the microcomputer 101 for processing. The microcomputer 101 may be provided with peripheral devices such as a CRT display 107 provided with a keyboard 108 and a plotter 109. Operator information for initiating and adjusting control of the probe survey can be input to the microcomputer 101 through the keyboard 108. The collected data, as processed by the microcomputer 101, can be visually displayed on the CRT 107 and/or plotted on the plotter 109. The collected data, either in its raw or processed form, can also be stored in the disk storage sub-system 106 for later use.

Thus, it will be appreciated that the present invention provides on-line real time display, recordal and analysis of the collected data. Accordingly, the system 100 could, within minutes, display profiles of topographic segments of the tube sheet. It will also be appreciated that the collected data could be transmitted from the microcomputer 101 via telephone lines or other means to a central facility for permanent retention of the data or for additional analysis.

From the foregoing, it can be seen that there has been provided an improved data collection system and probe positioning apparatus therefor which provides for fully automatic data collection after initial set-up of the system, the data being collected in a consistent, repeatable fashion without operator intervention. This system obviates the presence of operating personnel in the steam generator vessel, provides almost instantaneous identification, storage and reduction of the collected data and permits consistent interpretation and visualization of the data, in multiple format modes.

We claim:

1. Apparatus for positioning a probe within an enclosure defined by a vessel wall from outside the wall through an opening therein, said apparatus comprising: an elongated extensible boom having a longitudinal axis, said boom having an end adapted for longitudinal extension into and retraction from the enclosure through the opening therein; boom drive means coupled to said boom for effecting extension and retraction thereof; an elongated carrier extending along said boom from outside the vessel wall, said carrier being relatively rigid in the directions of its length and width and being relatively flexible in the direction of its thickness; feed means on said boom adjacent to said end thereof for longitudinally feeding said carrier from said boom independently of the movement of said boom in a feeding direction into the enclosure orthogonal to said axis, said feed means including means for deflecting said carrier into a path angularly disposed with respect to said axis, and tractor means engageable with said carrier for feeding said carrier in said feeding direction through said deflecting means; withdrawal means disposed outside the vessel wall for moving said carrier longitudinally in a withdrawing direction opposite to said feeding direction independently of the movement of said boom; a probe supported by said carrier at one end thereof; swivel means including an internally-toothed ring gear fixedly mounted on said feed means, and a drive gear mounted on said boom and disposed in meshing engagement with said ring gear, said swivel means effecting bidirectional rotational movement of said feed means about an axis parallel to said longitudinal axis thereby to permit positioning of said probe, first measuring means for measuring the movement of sais boom; second measuring means for measuring the movement of said carrier with respect to said boom, each of said first and second measuring means including a rotary resolving means for converting a linear distance into a corresponding rotational angle, said second measuring means including two measuring devices respectively associated with said feed means and said withdrawal means for respectively measuring movement of said carrier in said feeding direction and said withdrawing direction; third measuring means for measuring the angle through which said feed means is rotated by said swivel means; and a microcomputer system for processing the measurements of said first and second and third measuring means for accurately determining the position of said probe within the enclosure.

* * * * *